United States Patent [19]
Azuma et al.

[11] Patent Number: 4,459,284
[45] Date of Patent: Jul. 10, 1984

[54] PERMANENT WAVING COMPOSITION COMPRISING AMINO ACIDS

[75] Inventors: Tanehiko Azuma, Osaka; Kiyofumi Wakui, Nara; Nakatomi Fukuda, Kadoma; Yukio Sugihara, Suita, all of Japan

[73] Assignee: Nikko Pharmaceutical Co., Ltd., Osaka, Japan

[21] Appl. No.: 271,923

[22] Filed: Jun. 9, 1981

[30] Foreign Application Priority Data

Jul. 10, 1980 [JP] Japan .................. 55-94881

[51] Int. Cl.³ .......................... A61K 7/09; A61K 7/11
[52] U.S. Cl. ......................................... 424/72; 424/71
[58] Field of Search .................... 424/72, 71

[56] References Cited

U.S. PATENT DOCUMENTS 3,823,232  7/1974  Galerne ................................ 424/72

FOREIGN PATENT DOCUMENTS 210071  7/1960  Austria ................................ 424/72
797167  6/1958  United Kingdom .................. 424/72

Primary Examiner—Jerome D. Goldberg
Assistant Examiner—Freda Abramson
Attorney, Agent, or Firm—Wenderoth, Lind & Ponack

[57] ABSTRACT

Permanent waving composition containing thioglycolic acid or a salt thereof, and an acidic and/or neutral amino acid.

2 Claims, No Drawings

PERMANENT WAVING COMPOSITION COMPRISING AMINO ACIDS

The present invention relates to a novel permanent waving compositon.

Today, permanent waving is, in general, carried out by breaking down the cystine linkage in keratin of the hair with a first solution containing thioglycolic acid as a main component, and subsequent oxidation with a second solution containing bromate as a main component. However, in such a permanent waving treatment, since the thioglycolic acid or its salt used as the main component of the first solution is a very active chemical to both hair and skin, it often causes, even at its usually used relatively low concentration of about 6 to 7 w/w% in the first solution, worn-out and discolored hairs or eruption of head skin. Furthermore, the bromate used as the main component of the second solution is, as well known, an awkward and very oxidative chemical and therefore, it may cause falling-off of hair and impediments in the skin by the promotion of abovesaid undesirable effects of thioglycolic acid. In a permanent waving treatment with such first and second solutions, there is also such trouble that it requires rather complicated operations and a lengthy time and therefore, will cause considerable discomfort to the person receiving the treatment.

On the other hand, there is another permanent waving treatment using only the abovementioned first solution and no second solution. This method utilizes an air-oxidation in place of chemical oxidation with bromate in the second solution. However, since the hair cannot be subjected, while in an unstable reduced condition, to air oxidation for a longer period of time, it is necessary that the concentration of thioglycolic acid or its salt be lowered, thereby attaining a moderated reducing power against the cystine linkage in hair keratin. Therefore, in contrast with the treatment using the combination of abovementioned first and second solutions, the injurious actions to hair and skin are indeed decreased, but the main effects of the thioglycolic acid, i.e. wave formation and wave retaining power, are remarkably reduced.

The inventors, after lengthy consideration of these matters, have found that when an acidic amino acid and/or neutral amino acid are/is added, in a specified amount, to the first permanent waving solution containing as a main component thioglycolic acid or its salt, the injurious actions of the thioglycolic acid to hair and head skin, i.e. side-effects, are remarkably decreased and furthermore, long-lasting, soft and brilliant waves are formed in a shorter period of time with air-oxidation only, without using the second treatment solution.

The present invention provides, based on the abovesaid findings, a novel permanent waving composition which comprises thioglycolic acid or its salt as a main component, and an acidic and/or neutral amino acid. The present composition can give highly stable and sound wave formation and wave retaining effects, because there is no necessity to conduct the treatment with the second solution.

As the acidic amino acid which is to be used according to the invention to increase the main effects of thioglycolic acid and decrease the side effects thereof, mention is made of aspartic acid, glutamic acid and the like, and as the neutral amino acid, glycine, alanine, threonine, serine and the like. Particular preference is given to such members as having a hydroxyl group in its molecule, as, for example, serine and threonine. These acidic and neutral amino acids may be used in the form of a mixture of two or more, and in this case, preference is given to 1:3 to 3:1 mixture by moles of the acidic and neutral amino acids and especially of aspartic acid and threonine. These acidic or neutral amino acids may be used in either optically active form or a racemic mixture, and in the form of either free acid or appropriate salt as, for example, alkali metal salt such as potassium and sodium salts, triethylamine salt, triethanolamine salt, ammonium salt and the like. In either case, it is expected to increase the main effects and decrease the side effects of the thioglycolic acid.

The present permanent waving composition may be prepared, for example, by dissolving abovesaid acidic or neutral amino acid into an aqueous solution containing thioglycolic acid or its salt. Thioglycolic acid or its salt is usually used in a concentration ranging from about 2.5 w/v% to about 7.0 w/v%. Since too low a concentration may cause a decrease in wave formation and wave retaining powers and too high a concentration may cause an increase of injurious action of thioglycolic acid and a decrease in wave retaining power, the abovesaid concentration range, and especially 3 to 6 w/v%, is preferred. It is also proper to use the acidic or neutral amino acid in an amount of about 0.03 to 3 moles, preferably 0.3 to 1.5 moles, per mole of thioglycolic acid. In this case, pH of the solution is preferably adjusted to about 8 to 10, especially 9.0 to 9.5, with an organic base such as monoethanolamine, diethanolamine and triethanolamine, an alkali hydroxide such as potassium hydroxide and sodium hydroxide, and ammonia water or the like.

The present waving composition may include, for the purpose of improving waving performance, a wetting agent such as polypropyleneglycol, butyleneglycol, polyethyleneglycols and glycerine, a waving power increasing agent such as urea and ammonium thiocyanate, a surface active agent such as higher alcohol ether and higher fatty acid ester, various fats and oils, higher alcohol and the like, as well as hair tonics, coloring agents, perfumes and others.

With the present permanent waving composition, it is possible to markedly relieve the discomfort previously associated with a lengthy treatment, because a rapid waving operation is feasible with air oxidation only and without using a second solution containing as a main component a strong oxidizing agent such as bromate. The invention also makes it possible to conduct an excellent permanent waving treatment, in respect of wave forming and wave retaining powers, even with a composition having a lower thioglycolic acid concentration, because the acidic or neutral amino acid may increase the principal action of thioglycolic acid and decrease the side-effects thereof. It is also possible to carry out a safe waving treatment even with composition having a higher thioglycolic acid concentration.

The invention shall now be more fully explained in the following Experiments and Examples.

EXPERIMENT 1

A sample of human hair was treated with a one-step permanent waving solution prepared according to the following recipe, and diameters of curls thus formed were measured to determine the wave forming power of the solution. Wave retention was also determined by subjecting thus obtained curls to drastic treatment under conditions hereinunder stated.

1. Wave forming power test (a) Preparation of permanent wave solution (1) The prescribed amounts of 50% ammonium thioglycolate were dissolved in about 50 ml of distilled water, and to this concentrated ammonia water was added to adjust the pH to about 9.3. The prescribed amounts of amino acid were then dissolved in this solution, pH was again adjusted to 9.5 by the addition of concentrated ammonia water and distilled water was then added to make the total volume to 100 ml.

(2) The control permanent waving solution was prepared as in (1) except that the amino acid was omitted therefrom.

(b) Test samples

Each 0.5 g of human hair (about 15 cm length) was bound to make a bundle of hairs, which was washed with aqueous 1.0% sodium lauryl sulfate solution and left to dry at room temperature to make sample hairs.

(c) Test method

Sample hairs were wound on plastic rods each having a diameter of 0.9 cm and the wound hairs were coated well with permanent waving solution and left to stand at room temperature for 20 minutes. Thereafter, they were, while being wound on the rods, washed well with water and left to stand at room temperature for 20 minutes. The hairs were removed from the rods, and rinsed with running water and left to dry at room temperature. The abovesaid experiments were repeated 6 times for the respective recipe and after each time, curl diameters after said drying were recorded. The mean curl diameter obtained was used as mean wave value in expressing the wave forming power.

2. Wave retention test

After measuring the curl diameters in (1), the hairs were dipped into an aqueous 5% sodium lauryl sulfate solution (50° C.) and stirred for 30 minutes. The hairs were taken out and washed well with running water, left to dry at room temperature and measured again for diameters of the curls. The mean diameter value was used for judging wave retention.

3. Test results

The results obtained are shown in Table 1.

TABLE 1

| Exper. No. | Added amino acid | | thioglycolic acid (w/v %) | wave forming power (cm) | wave retention (cm) |
|---|---|---|---|---|---|
| | amino acid | molar ratio* | | | |
| Permanent waving composition of the present invention | | | | | |
| 1 | L-threonine | 0.03 | 3 | 2.07 | 2.82 |
| 2 | | 0.15 | 3 | 2.08 | 2.97 |
| 3 | | 0.3 | 3 | 2.08 | 2.72 |
| 4 | | 1.5 | 3 | 2.00 | 3.03 |
| 5 | L-Aspartic | 0.03 | 3 | 2.10 | 3.07 |
| 6 | acid | 0.15 | 3 | 1.97 | 2.93 |
| 7 | | 0.3 | 3 | 1.98 | 2.72 |
| 8 | | 1.5 | 3 | 2.23 | 3.03 |
| 9 | DL-Serine | 0.15 | 3 | 2.07 | 2.93 |
| 10 | | 0.3 | 3 | 2.12 | 2.75 |
| 11 | | 1.5 | 3 | 2.20 | 3.00 |
| 12 | L-Glutamic | 0.15 | 3 | 1.95 | 2.95 |
| 13 | acid | 0.3 | 3 | 2.05 | 2.68 |

TABLE 1-continued

| Exper. No. | Added amino acid | | thioglycolic acid (w/v %) | wave forming power (cm) | wave retention (cm) |
|---|---|---|---|---|---|
| | amino acid | molar ratio* | | | |
| 14 | | 1.5 | 3 | 2.23 | 3.03 |
| Control | — | — | 3 | 2.43 | 3.58 |

*molar ratio against thioglycolic acid (hereinafter the same)

EXPERIMENT 2

By the same procedures as stated in Experiment 1, the wave forming powers and wave retentions were determined for the waving compositions containing the amino acids listed in Table 2 and prepared as in Experiment 1 except that the concentration of thioglycolic acid was changed to 4.5 w/v%. The results are shown in Table 2.

TABLE 2

| Exper. No. | Added amino acid | | thioglycolic acid (w/v %) | wave forming power (cm) | wave retention (cm) |
|---|---|---|---|---|---|
| | amino acid | molar ratio* | | | |
| Permanent waving composition of the present invention | | | | | |
| 1 | L-threonine | 0.03 | 4.5 | 1.78 | 2.60 |
| | | 0.15 | 4.5 | 1.77 | 2.48 |
| | | 0.3 | 4.5 | 1.77 | 2.35 |
| | | 1.5 | 4.5 | 1.92 | 2.68 |
| 2 | L-aspartic | 0.03 | 4.5 | 1.73 | 2.65 |
| | acid | 0.15 | 4.5 | 1.80 | 2.58 |
| | | 0.3 | 4.5 | 1.75 | 2.45 |
| | | 1.5 | 4.5 | 1.88 | 2.72 |
| 3 | DL-serine | 0.15 | 4.5 | 1.77 | 2.60 |
| | | 0.3 | 4.5 | 1.80 | 2.53 |
| | | 1.5 | 4.5 | 2.00 | 2.78 |
| 4 | L-glutamic | 0.15 | 4.5 | 1.88 | 2.65 |
| | acid | 0.3 | 4.5 | 1.85 | 2.58 |
| | | 1.5 | 4.5 | 2.03 | 2.78 |
| Control | — | — | 4.5 | 2.05 | 3.13 |

EXPERIMENT 3

By the same procedures as stated in Experiment 1, wave forming powers and wave retentions were determined for the waving compositions containing the amino acids listed in Table 3, prepared as in Experiment 1 except that the concentration of thioglycolic acid was changed to 6 w/v%. The results are shown in Table 3.

TABLE 3

| Exper. No. | Added amino acid | | thioglycolic acid (w/v %) | wave forming power (cm) | wave retention (cm) |
|---|---|---|---|---|---|
| | amino acid | molar ratio* | | | |
| Permanent waving composition of the present invention | | | | | |
| 1 | L-threonine | 0.03 | 6 | 1.67 | 2.53 |
| | | 0.15 | 6 | 1.67 | 2.42 |
| | | 0.3 | 6 | 1.70 | 2.40 |
| | | 1.5 | 6 | 1.67 | 2.72 |
| 2 | DL-aspartic | 0.03 | 6 | 1.60 | 2.62 |
| | acid | 0.15 | 6 | 1.63 | 2.37 |
| | | 0.3 | 6 | 1.65 | 2.40 |
| | | 1.5 | 6 | 1.68 | 2.77 |
| 3 | DL-serine | 0.15 | 6 | 1.67 | 2.42 |
| | | 0.3 | 6 | 1.68 | 2.42 |
| | | 1.5 | 6 | 1.65 | 2.70 |

TABLE 3-continued

| Exper. No. | Added amino acid | | thiogly-colic acid (w/v %) | wave forming power (cm) | wave retention (cm) |
| --- | --- | --- | --- | --- | --- |
| | amino acid | molar ratio* | | | |
| 4 | L-glutamic acid | 0.15 | 6 | 1.63 | 2.43 |
| | | 0.3 | 6 | 1.67 | 2.40 |
| | | 1.5 | 6 | 1.70 | 2.80 |
| Control | — | — | 6 | 1.60 | 3.40 |

EXPERIMENT 4

By the same procedures as stated in Experiment 1, wave forming powers and wave retentions were determined for the waving compositions prepared as in Experiment 1, but containing a mixture of amino acids listed in Table 4, each in a prescribed molar ratio. Thus obtained results are shown in Table 4.

TABLE 4

| Exper. No. | Added amino acid | | thiogly-colic acid (w/v %) | wave forming power (cm) | wave retention (cm) |
| --- | --- | --- | --- | --- | --- |
| | amino acid | molar ratio | | | |
| Permanent waving composition of the present invention | | | | | |
| 1 | L-threonine | 0.075 | 3 | 2.00 | 2.68 |
| | L-aspartic acid | 0.225 | | | |
| 2 | L-threonine | 0.10 | 3 | 1.97 | 2.72 |
| | L-aspartic acid | 0.20 | | | |
| 3 | L-threonine | 0.15 | 3 | 1.95 | 2.67 |
| | L-aspartic acid | 0.15 | | | |
| 140 | L-threonine | 0.20 | 3 | 1.90 | 2.65 |
| | L-aspartic acid | 0.10 | | | |
| 5 | L-threonine | 0.225 | 3 | 1.90 | 2.65 |
| | L-aspartic acid | 0.075 | | | |
| Control | — | — | 3 | 2.43 | 3.58 |

EXPERIMENT 5

A sample of hair was treated with one-step and two-step permanent waving solutions of the following recipes and changes on standing of thus formed waves were compared. The results are shown in Table 5.

(a) Permanent waving solutions

| (Recipe) | | recipe | Added amino acid | | thioglycolic acid (w/v %) |
| --- | --- | --- | --- | --- | --- |
| | | | amino acid | molar ratio | |
| Permanent waving composition of the present invention | | | | | |
| | one-step | A | L-threonine | 0.3 | 3 |
| | one-step | B | L-aspartic acid | 0.3 | 3 |
| control | one-step | C | — | — | 3 |
| control | two-step | D** | — | — | 3 |

**D shows only the prescription of the first solution of two-step permanent waving composition.

Using the above mentioned components, permanent waving solutions were prepared as in Experiment 1. In the case of recipe D, aqueous 6% sodium bromate solution was used as the second permanent waving solution.

(b) Test samples

The same materials as stated in Experiment 1 were used.

(c) Test methods (1) One-step permanent waving solution was tested in the same way as stated in Experiment 1.

(2) Two-step permanent wave solution:

Sample hairs were wound on plastic rods each having a diameter of 0.9 cm and the wound hairs were coated well with the first permanent waving solution and left to stand at room temperature for 20 minutes. Then, after rinsing with water, the second permanent waving solution was applied and the hairs were left to stand at room temperature for an additional 20 minutes. The hairs were removed from the rods and washed and left to dry at room temperature. The curl dimensions of thus formed, waved hairs were measured and the same experiments were repeated 6 times. The mean curl diameter obtained was used as a measure for representing curl forming power. Thereafter, the curled hairs were hung on pegs and left standing at room temperature for a defined period of time. The curl diameters were then measured and the mean curl diameter was used for comparison in the column of "change on standing" in Table 5.

TABLE 5

| Exper. No. | Recipe | change on standing | | | |
| --- | --- | --- | --- | --- | --- |
| | | after treatment | 1 day after | 7 days after | 30 days after |
| Permanent waving composition of the present invention | | | | | |
| 1 | A | 2.07 | 2.47 | 2.52 | 2.60 |
| 2 | B | 2.03 | 2.50 | 2.57 | 2.57 |
| Control | | | | | |
| 3 | C | 2.45 | 2.92 | 3.23 | 3.35 |
| 4 | D | 1.98 | 2.40 | 2.55 | 2.63 |

From the above, it is clear that the present one-step permanent waving solution is superior to the control one-step permanent waving solution in both respects of wave forming power and wave retention, and that it has the same degree of wave forming power as that of the two-step permanent waving composition, but is rather superior to the same in respect of wave retention.

EXAMPLE 1

| Recipe | |
| --- | --- |
| Ammonium thioglycolate (50% aqueous solution) | 6.0 g |
| L-threonine | 1.2 g |
| Polyoxyethylene lanolin | 0.3 g |
| conc. ammonia water | 2.0 g |
| Coloring material | 0.1 g |
| Perfume | appropriate amount |

The abovesaid components were dissolved in distilled water to make 100 ml and to this, was added conc. ammonia water to adjust the pH to 9.5, thereby obtaining a one-step permanent waving solution.

EXAMPLE 2

| Recipe | |
| --- | --- |
| Thioglycolic monoethanolamine (50% aqueous solution) | 6.0 g |
| L-Aspartic acid | 1.3 g |
| Monoethanolamine | 2.0 g |
| Gelatin | 0.5 g |
| Polyoxyethylene cetyl ether | 0.5 g |
| Coloring material | 0.1 g |
| Perfume | appropriate amount |

The abovesaid components were dissolved in distilled water to make 100 ml and to this, was added monoethanolamine to adjust the pH to 9.5, thereby obtaining a one-step permanent waving solution.

EXAMPLE 3

| Recipe | |
| --- | --- |
| Ammonium thioglycolate (50% aqueous solution) | 6.0 g |
| L-Threonine | 3.6 g |
| Polyoxyethylene monostearate | 0.5 g |
| conc. ammonia water | 2.0 g |
| Coloring material | 0.1 g |
| Perfume | appropriate amount |

The abovesaid components were dissolved in distilled water to make 100 ml and to this, was added diluted ammonia water to adjust the pH to 9.5, thereby obtaining a one-step permanent waving solution.

EXAMPLE 4

| Recipe | |
| --- | --- |
| Ammonia thioglycolate (50% aqueous solution) | 9.0 g |
| L-Aspartic acid | 4.0 g |
| Diethanolamine | 2.0 g |
| Urea | 1.0 g |
| Polyoxyethylene lauryl ether | 0.5 g |
| Coloring material | 0.1 g |
| Perfume | appropriate amount |

The abovesaid components were dissolved in distilled water to make 100 ml and to this, was added conc. ammonia water to adjust the pH to 9.5, thereby obtaining a one-step permanent waving solution.

EXAMPLE 5

| Recipe | |
| --- | --- |
| Ammonium thioglycolate (50% aqueous solution) | 6.0 g |
| DL-Serine | 1.1 g |
| conc. ammonia water | 2.0 g |
| Polyoxyethylene cetyl ether | 0.2 g |
| Cetanol | 1.0 g |
| Coloring material | 0.1 g |
| Perfume | appropriate amount |

The abovesaid components were dissolved in distilled water to make 100 ml and to this, was added conc. ammonia water to adjust the pH to 9.5, thereby containing a one-step permanent waving solution.

EXAMPLE 6

| Recipe | |
| --- | --- |
| Thioglycolic monoethanolamine (50% aqueous solution) | 6.0 g |
| L-Glutamic acid | 1.5 g |
| Triethanolamine | 2.0 g |
| Polyoxyethylene oleyl ether | 0.2 g |
| Glycerin | 2.0 g |
| Coloring material | 0.1 g |
| Perfume | appropriate amount |

The abovesaid components were dissolved in distilled water to make 100 ml and to this, was added conc. ammonia water to adjust the pH to 9.5, thereby obtaining a one-step permanent waving solution.

EXAMPLE 7

| Recipe | |
| --- | --- |
| Ammonium thioglycolate (50% aqueous solution) | 6.0 g |
| L-Glutamic acid | 1.1 g |
| DL-Serine | 0.3 g |
| Polyoxyethylene monostearate | 0.5 g |
| conc. ammonia water | 1.5 g |
| Coloring material | 0.1 g |
| Perfume | appropriate amount |

The abovesaid components were dissolved in distilled water to make 100 ml and to this, was added diluted ammonia water to adjust the pH to 9.5, thereby obtaining a one-step permanent waving solution.

EXAMPLE 8

| Recipe | |
| --- | --- |
| Ammonium thioglycolate (50% aqueous solution) | 9.0 g |
| L-Threonine | 1.2 g |
| L-Glutamic acid | 1.5 g |
| Monoethanolamine | 1.5 g |
| Stearyl trimethyl ammonium chloride | 0.5 g |
| Polyoxyethylene lauryl ether | 1.0 g |
| Propyleneglycol | 2.0 g |
| Polyoxyethylene lanolin | 0.5 g |
| Perfume | appropriate amount |

The abovesaid components were dissolved in distilled water to make 100 ml and to this, was added diluted ammonia water to adjust the pH to 9.3, thereby obtaining a one-step permanent waving solution.

EXAMPLE 9

| Recipe | |
| --- | --- |
| Ammonium thioglycolate (50% aqueous solution) | 9.0 g |
| L-Aspartic acid | 1.0 g |
| Glycine | 0.2 g |
| Triethanolamine | 3.0 g |
| Benzalkonium chloride solution (50%) | 1.0 g |
| Polyoxyethylene hydrogenated castor oil | 0.3 g |
| Glycerin | 2.0 g |
| Perfume | appropriate amount |

The abovesaid components were dissolved in distilled water to make 100 ml and to this, was added diluted ammonia water to adjust the pH to 9.0, thereby obtaining a one-step permanent waving solution.

What we claim is:

1. An aqueous composition for permanently waving hair, which comprises 3 to 6 w/v % of ammonium thioglycolate, and an amino acid component selected from the group consisting of aspartic acid, threonine and a mixture of aspartic acid and threonine wherein the molar ratio of the aspartic acid to the threonine in said mixture is 1:3 to 3:1, the amount of the amino acid component being 0.3 to 1.5 moles per mole of the ammonium thioglycolate, the pH of the composition being 9.0–9.5.

2. A composition as claimed in claim 1 wherein said amino acid component is said mixture of aspartic acid and threonine.

* * * * *